United States Patent [19]

George

[11] 4,454,868

[45] Jun. 19, 1984

[54] LOW FORCE SKELETAL ADJUSTING DEVICE

[75] Inventor: Phillip E. George, Rock Island, Ill.

[73] Assignee: Specialty Devices, Inc., Davenport, Iowa

[21] Appl. No.: 365,524

[22] Filed: Apr. 5, 1982

[51] Int. Cl.³ .................... A61F 5/00

[52] U.S. Cl. .................... 128/69; 128/67

[58] Field of Search .................... 128/28, 30.2, 38–40, 128/54–55, 60, 61, 67, 69; D24/36, 41

[56] References Cited

U.S. PATENT DOCUMENTS

| | | | |
|---|---|---|---|
| D. 204,581 | 4/1966 | Coulson | D24/36 |
| 1,714,557 | 5/1929 | Haslett | 128/67 |
| 1,973,768 | 9/1934 | Knapp | 128/54 |
| 3,051,980 | 9/1962 | Rosenthal | 128/67 X |
| 4,126,129 | 11/1976 | Rainbow | 128/67 |

FOREIGN PATENT DOCUMENTS

| | | | |
|---|---|---|---|
| 575346 | 7/1924 | France | 128/32 |

*Primary Examiner*—Richard J. Apley
*Assistant Examiner*—David J. Brown
*Attorney, Agent, or Firm*—Jeffrey J. Miller

[57] ABSTRACT

A low force skeletal adjusting device comprises a first elastomeric member having a surface for contacting the hand. Said surface located opposite a surface for contacting a selected portion of the anatomy. Said elastomeric member is retained within a solid rigid member to provide support therefor. The surface for contacting the hand is substantially larger in diameter than the surface for contacting the anatomy thus, the force per unit area applied to the surface for contacting the hand is substantially less than the force per unit area applied to the selected anatomy by the surface for contacting same. Therefore, the requisite therapeutic force can be advantageously controlled to a fine degree.

11 Claims, 6 Drawing Figures

FIG. 2
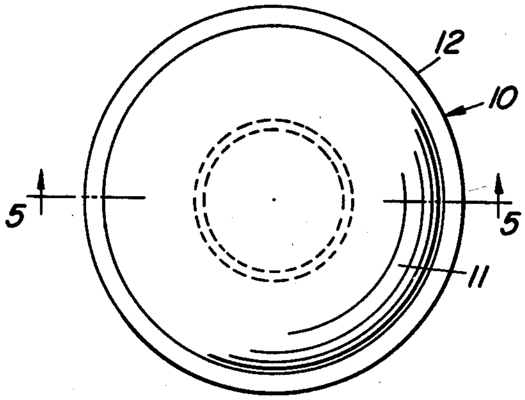
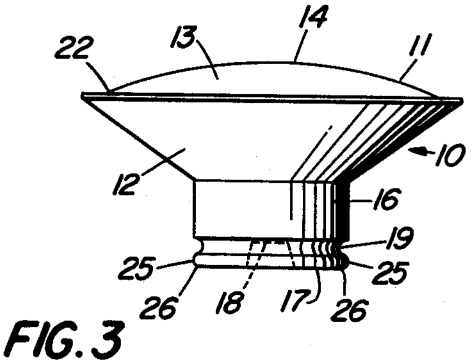
FIG. 3
FIG. 5
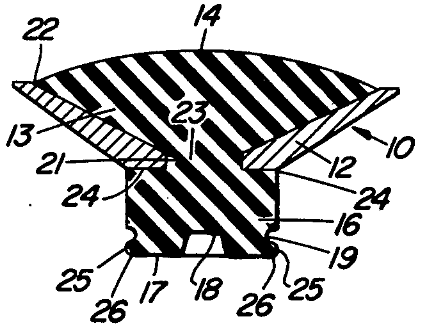
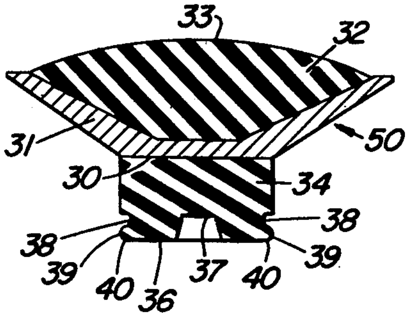
FIG. 6
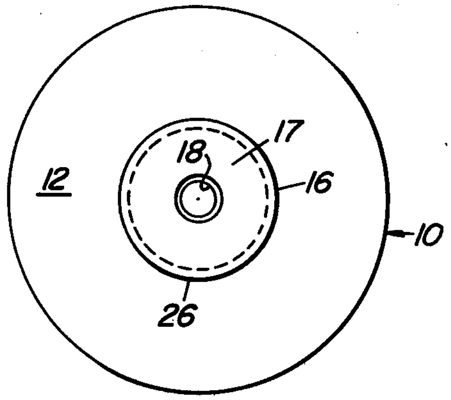
FIG. 4

LOW FORCE SKELETAL ADJUSTING DEVICE

BACKGROUND OF THE INVENTION

1. Field of the Invention

This invention relates to devices for aiding skeletal adjustment and, more particularly to a device requiring low manual forces to accomplish the therapeutic adjustment.

2. Description of the Prior Art

The traditional basis for chiropractic involves manual adjustment of the various components of the human anatomy with particular attention paid to the skeleton and especially the spinal vertebrae. Various techniques for accomplishing traditional chiropractic adjustments include the use of drop mechanisms, pre-osseous stressing and induction of rotation of the anatomy of interest and related skeletal structures. These techniques require either sophisticated and expensive equipment or alternatively utilize techniques which may cause undue discomfort to the patient and increase likelihood of iatrogenic injury.

It is, therefore, desirable to provide a device which avails the chiropractor with a means for accomplishing spinal adjustment without the use of specialized equipment or techniques which may result in injury to the patient.

SUMMARY OF THE INVENTION

There is, therefore, provided in the practice of this invention according to a presently preferred embodiment, a device for application of force via the human hand to selected areas of human anatomy. The device is comprised of an elastomeric member having a first surface for contacting the hand and a second surface for contacting the anatomy, said surfaces are disposed at opposite ends of the elastomeric member. The device additionally comprises a hollow rigid member having first and second openings, said elastomeric member being disposed within and extending through the rigid member to provide support therefor.

BRIEF DESCRIPTION OF THE DRAWINGS

These and other features and advantages of the present invention will be better understood by reference to the following detailed description when considered in connection with the accompanying drawings wherein:

FIG. 2 is a top view of the device;

FIG. 3 is a side elevation of the device;

FIG. 4 is bottom view of the device;

FIG. 5 is a cross sectional view of the device shown in FIG. 2 on line 5—5;

FIG. 6 is a cross sectional view of an alternative embodiment of a device constructed according to the principles of this invention.

DESCRIPTION OF THE PREFERRED EMBODIMENTS

Figure 1:
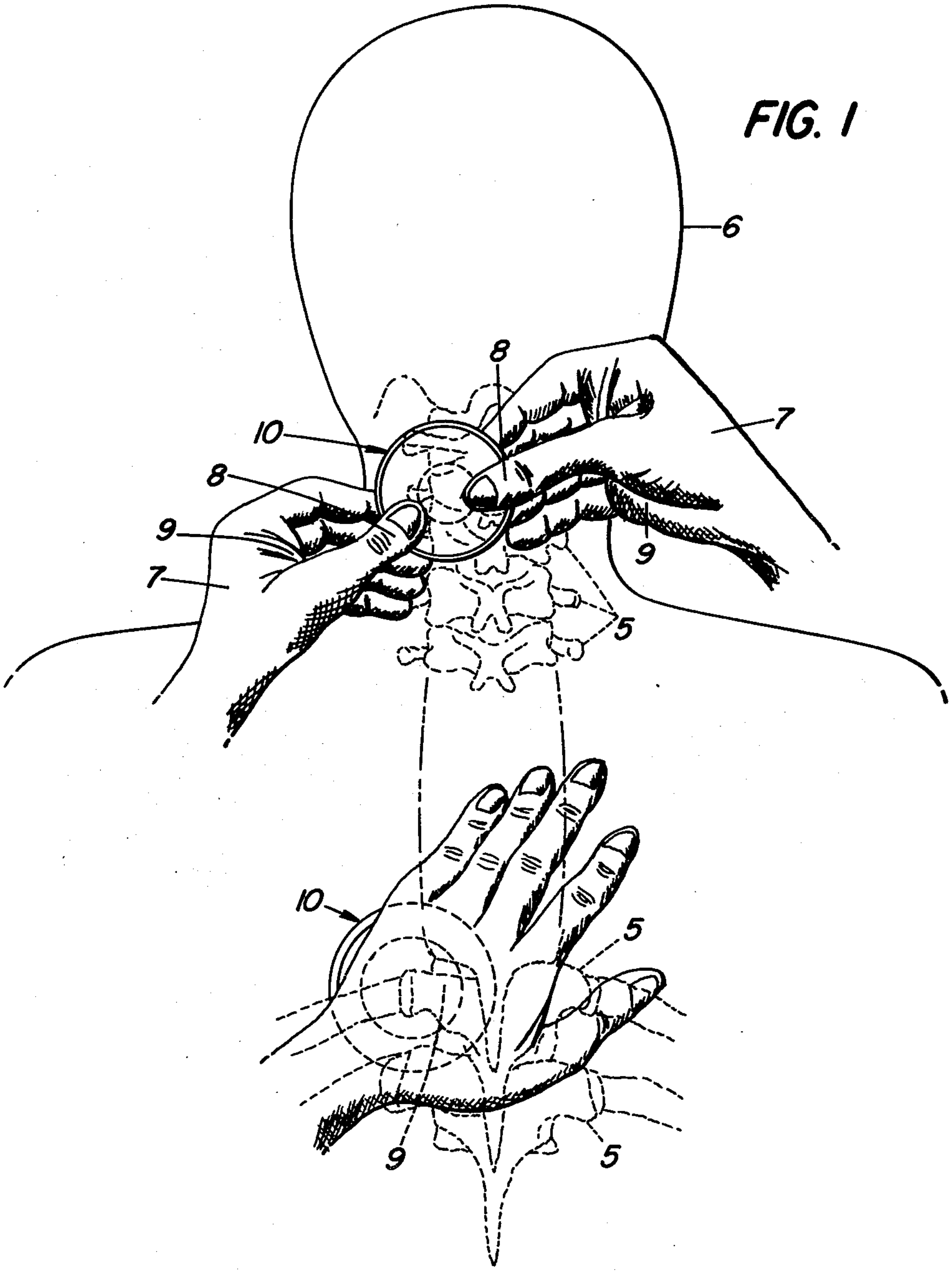
FIG. 1 illustrates the use of the device constructed according to the principles of this invention.

FIG. 1 illustrates a person using an adjusting device 10 constructed according to the principles of this invention. Common pathology relating to dysfunction of the spinal column includes fixations of the spinal vertebrae 5 which can result in alteration of spinal reflexes, restraint of functioning of the anatomy to a normal excrusion or articular range of motion and imbalance of neuromuscular tension.

A common therapeutic method for treating these fixations includes adjusting the spinal vertebrae utilizing manual manipulation in conjunction with special tables having drop mechanisms. These manual adjustments may also include pre-osseous stressing or induction of rotation of the anatomy of interest.

The technique utilizing the adjusting device constructed according to the principles of this invention alleviates fixation of the vertebral segment in question by specifically and selectively cleaving the vertebrae. The use of the adjusting device also enhances, speed, direction, velocity and specificity of the therapeutic maneuvers while utilizing substantially less force than would otherwise be required.

As illustrated and hereinabove described the adjusting device 10 is placed in contact with the patient's 6 spinal vertebrae 5 of interest by the practioner who applies force with either has thumbs 8 or the palm 9 of his hand 7.

In the preferred embodiment shown in FIGS. 2, 3, 4 and 5 the adjusting device 10 comprises an elastomeric member 11 which is conveniently and economically formed of silicone rubber or styrene-butadiene rubber or the like. Alternatively, said elastomeric member 11 can be comprised of natural rubbers, cis-polybutadiene rubbers, cis-polyisoprene rubbers, ethylene-propalene rubbers, butyl rubbers, polyacrylates, polysulfide rubbers, florocarbons, neoprene, nitrile rubbers, and polyurethanes.

In the preferred embodiment the elastomeric member 11 is comprised of three geometric elements molded into a single piece. The first element is a truncated cone 13 the base of which comprises a first surface 14 which is convex for mating with the thumbs or palm of the hand. A first cylindrical element 16 one end of which comprises a second surface 17 for contacting the anatomy of interest has a circular depression 18 centrally disposed on said contacting surface 17 and additionally has a groove 19 disposed circumferentially in proximity to the end of the cylinder comprising the surface 17 for contacting the anatomy. Disposed between the truncated conical element 13 and the first cylindrical element 16 is a second cylindrical element 21 having a diameter substantially less than that of the diameter of the first cylindrical element 16.

A hollow rigid member 12 is preferrably constructed of aluminum or similar rigid material and comprises a truncated cone having a first circular opening 22 at the base of the cone wherein the truncated conical element 13 of the elastomeric member 11 is cooperatively disposed. A second opening 23 at the truncated end of the rigid member 12 has the second cylindrical element 21 of the elastomeric member 11 disposed therein. The second opening 23 also provides an annular seating surface 24 upon which a portion of the first cylindrical element 16 of the elastomeric member rests.

The device is constructed by selecting suitable diameters for the second opening 23 and the first cylindrical element 16 such that said element can be compressed to the degree necessary to permit it to be passed through the second opening 23 in a compressed state. Upon release of the compression, the cylindrical element 16 expands, thus, cooperatively retaining the elastomeric member 11 within the hollow rigid member 12. The second cylindrical element 21 is then seated in the second opening 23 of the rigid member 12.

In the preferred practice the adjusting device is used by applying force to the convex surface 14 of the elastomeric member 13 by use of the thumbs or palm of the hand. The force is then transmitted to the surface 17 for contacting the anatomy of interest. Due to the overall geometric shape of the adjusting device the force per unit area applied to the first surface 14 is increased by a proportion approximately equal to the surface area of the convex surface 14 divided by the surface area of the second surface 17 for contacting the anatomy. Thus, where substantial force would be required without the aid of the device of this invention, proportionately less force can be applied by the practioner to the device 10 to achieve the desired result. Consequently, the requisite therapeutic adjusting force can be carefully regulated by the practioner.

Typically, the ratio of the diameter of the convex surface 14 to the diameter of the contacting surface 17 lies in a range from about 2:1 to 8:1 resulting in a force per unit area increase from about 4 to 64 times.

Experience in utilizing the adjusting device of this invention dictates that the diameter of the contacting surface 17 must be matched to the specific anatomy of interest so that the maximum desired result is achieved. For example, the contacting surface utilized in adjusting thoracic vertebrae is dependent upon the size and frame of the patient but typically ranges from $\frac{3}{8}$" to $\frac{1}{2}$". A typical set of the devices constructed according to the principles of the invention includes devices having contacting surfaces 17 of approximately $\frac{3}{8}$", $\frac{1}{2}\frac{1}{2}$", $\frac{3}{4}$", 1" and 2" in diameter. Therefore, in the practice of this invention the practioner will have a set of adjusting devices constructed according to this invention where the contacting surfaces 17 are of varying diameters and the convex surfaces 14 are of concomitantly varying diameters to maintain the ratio of the surface area of the convex surface 14 to that of the contacting surface 17 in the range of approximately 4:1 to 64:1 times.

The elastic quality of the elastomeric member serves an important function in the practice of the adjusting device. Upon application of force to the convex surface 14, said member undergoes a degree of compression requisite to achieve the therapeutic result. Specifically, said compression of the elastomeric member 11 is released uniformly against the anatomy of interest via the contacting surface 17. Moreover, the elastic nature of the contacting surface 17 provides necessary conformity to the contacted anatomical structure such that the force applied by the practioner is uniformly applied to said structure.

The circular depression 18 and the circumferential groove 19 also serve a functional role in the therapeutic action of the adjusting device.

The groove 19 acts to limit the force applied to the anatomy at the edge 26 of the first cylindrical element 16. Thus, when force is applied to the device 10 the lip 25 so formed by the groove 19 is deformed toward the groove 19 and thus does not transmit force equal to that of the surface 17 immediately adjacent to the lip 25. Said deformation of the lip 25 provides a progressively decreasing continuum of force toward the outer edge 26 of the surface 17 thus, preventing tissue damage at said edge.

The circular depression 18 prevents the central portion of the contacting surface 17 from contacting the anatomy. Thus, soft tissue interposed between the contacting surface 17 and the skeletal element of interest is displaced into the depression 18. This displacement of the soft tissue helps to stablize the adjusting device during adjustment.

FIG. 6 shows a cross section of an alternative embodiment 50 of the invention described herein, a hollow rigid member 31 comprises a truncated cone which is closed at the truncated end. A first elastomeric member 32 is a solid truncated cone cooperatively disposed within the hollow rigid member 31. The conical member 32 is adhesively attached to the inner surface of the rigid member 31. A convex surface 33 is formed by the base of the elastomeric member 32 for contacting the palm of the hand or thumbs.

A cylindrical elastomeric member 34 is adhesively attached to the base 30 of the hollow rigid member. The circular surface 36 opposite that attached to the rigid member 31 is provided for contacting the anatomy of interest. Said surface 36 has a centrally disposed depression 37 and a groove 38 disposed circumferentially in proximity to said surface 36 for contacting the anatomy. Said groove 38 defines a lip 39 which has an outer edge 40.

Use of the alternative embodiment is identical to that of the preferred embodiment. Additionally, each element of the structure of the alternative embodiment has a function analogous to the corresponding element of the preferred embodiment.

The described embodiments of the invention are only considered to be preferred and illustrative of the inventive concept; the scope of the invention is not be restricted to such embodiments. Various and numerous other arrangements may be devised by one skilled in the art without departing from the spirit and the scope of this invention. For example, the elastomeric member 11 may be adhesively attached to the rigid member 12 in the preferred embodiment. This type of arrangement for fixing the elastomeric member 11 in the rigid member 12 would obviate the necessity of having a first cylindrical element 16 with a larger diameter than the second opening 23 in the rigid member 12.

Additionaly the height of the second cylindrical element 21 can be selected to be very small while still providing purchase means for the rigid member 12 at the second opening 23.

I claim:

1. A device for application of force by the human hand to selected areas of the human anatomy comprising:

an elastomeric member having a first surface for contacting the hand and a second surface for contacting the anatomy, said surfaces disposed at opposite ends of the elastomeric member; and a hollow rigid member having first and second openings, said elastomeric member being disposed within and extending through the rigid member.

2. The device of claim 1 wherein the hollow rigid member is a truncated cone having an opening at the base of the cone comprising said first opening of the rigid member and an opening at the truncated end of the cone comprising said second opening of the rigid member.

3. The device of claim 2 wherein the first surface for contacting the hand is disposed within the first opening of the rigid member and the second surface for contacting the anatomy is extended through the second opening of the rigid member.

4. The device of claim 1 whereiin the elastomeric member comprises:

a truncated conical element having a first end opposite the base of the cone, the base of the cone comprising the first surface of the elastomeric member;

a first cylindrical element, one end of which comprises the second surface of the elastomeric member; and a second cylindrical element disposed between the first cylindrical element and the first end of the conical element.

5. The device of claims 1 or 4 wherein the elastomeric member is an elastomer selected from the group consisting of: styrene-butadiene rubbers, natural rubber, cis-polybutadiene rubbers, cis-polyisoprene rubbers, ethylene-propylene rubbers, butyl, polysulfide rubbers, silicones, polyacrylates, fluorocarbons, neoprene, nitrile rubbers, polyurethanes.

6. The device of claims 1 or 4 wherein the first surface of the elastomeric member has a convex surface for mating with the hand.

7. The device of claims 1 or 4 wherein the second surface of the elastomeric member has a centrally disposed circular depression.

8. The device of claim 4 wherein the second opening of the rigid member is circular and has the second cylindrical element of the elastomeric member disposed therein.

9. The device of claim 4 wherein a groove is disposed circumferentially about the first cylindrical element of the elastomeric member in proximity to the end of said cylindrical element comprising the second surface of the elastomeric member.

10. A device for application of force by the human hand to selected areas of human anatomy comprising:

an elastomeric member having a truncated conical element, the base of which comprises a convex contacting surface for mating with the hand, a first cylindrical element one end of which comprises a surface for contacting the anatomy, said cylindrical element having a circular depression centrally disposed on said contacting surface and a groove disposed circumferentially in proximity to the end comprising said surface for contacting the anatomy, and a second cylindrical element disposed between the first cylindrical element and the truncated end of the conical element; and a hollow rigid member comprising a truncated cone having a first circular opening at the base wherein the truncated conical element of the elastomeric member is cooperatively disposed and a second circular opening at the truncated end of the cone wherein the second cylindrical element of the elastomeric member is disposed.

11. The device of claim 1, 4 or 10 wherein the area of the first surface for contacting the hand is approximately 4 to 64 times greater than the second surface for contacting the anatomy.

* * * * *